United States Patent
Kugler (10) Patent No.: US 8,022,397 B2
(45) Date of Patent: Sep. 20, 2011

(54) TRANSISTOR

(75) Inventor: Thomas Kugler, Cambridgeshire (GB)

(73) Assignee: Seiko Epson Corporation, Tokyo (JP)

( * ) Notice: Subject to any disclaimer, the term of this patent is extended or adjusted under 35 U.S.C. 154(b) by 491 days.

(21) Appl. No.: 12/155,741

(22) Filed: Jun. 9, 2008

(65) Prior Publication Data

US 2009/0039343 A1   Feb. 12, 2009

(30) Foreign Application Priority Data

Jun. 8, 2007   (GB) .................................. 0711075.2

(51) Int. Cl.
H01L 35/24 (2006.01)
H01L 51/00 (2006.01)

(52) U.S. Cl. .................................. 257/40; 257/E51.001
(58) Field of Classification Search .................... 257/40, 257/E51.001
See application file for complete search history.

(56) References Cited

U.S. PATENT DOCUMENTS

| | | | |
|---|---|---|---|
| 5,362,975 A * | 11/1994 | von Windheim et al. ....... | 257/76 |
| 6,833,059 B2 | 12/2004 | Kawarada | |
| 7,646,013 B2 * | 1/2010 | Herlogsson et al. ............ | 257/40 |
| 2002/0158295 A1 * | 10/2002 | Armgarth et al. ............. | 257/431 |
| 2002/0171081 A1 * | 11/2002 | Vincent et al. .................. | 257/40 |
| 2003/0052015 A1 * | 3/2003 | Becker et al. ................. | 205/414 |
| 2006/0202289 A1 | 9/2006 | Armgarth et al. | |
| 2006/0250558 A1 * | 11/2006 | Burns et al. ................... | 349/139 |

FOREIGN PATENT DOCUMENTS

| | | |
|---|---|---|
| EP | 1 786 049 A1 | 5/2007 |
| SE | 0100748-3 C2 | 6/2003 |
| WO | WO 02/071505 A1 | 9/2002 |
| WO | WO 03/047009 A1 | 6/2003 |

OTHER PUBLICATIONS

Kawai et al., "A Flexible 2-in. QVGA LTPS-TFT Electrophoretic Display," *SID International Symposium, Seminar and Exhibition*, Boston, 2005, pp. 1638-1641.
Tam et al., "The Design and Driving of Active-Matrix Electrochromic Displays Driven by LTPS TFTs," *SID International Symposium, Seminar and Exhibition*, San Francisco, 2006, pp. 33-36.
Veres et al., "Low-$k$ Insulators as the Choice of Dieletrics in Organic Field-Effect Transistors," *Advanced Functional Materials*, vol. 13, No. 3, Mar. 2003, pp. 199-204.
Elschner, "High conductive PEDOT/PSS—a polymeric alternative to inorganic TCOs," $XIII^{th}$ *International Seminar: Commercial Application of Conductive Polymers*, Florence, Italy, Oct. 9-11, 2006.

(Continued)

*Primary Examiner* — Eugene Lee
*Assistant Examiner* — Anthony Ho
(74) *Attorney, Agent, or Firm* — Oliff & Berridge, PLC (57) ABSTRACT

An electrolyte-gated field effect transistor is disclosed, the transistor comprising an electrolyte including a polymeric ionic liquid analogue. In a preferred embodiment, the transistor further comprises a source electrode, a drain electrode disposed so as to be separated from the source electrode, forming a gap between the source and drain electrodes, a semiconductor layer bridging the gap between the source and drain electrodes and thus forming a transistor channel, and a gate electrode positioned so as to be separated from the source electrode, the drain electrode and the semiconductor layer. In this embodiment, the electrolyte is disposed so as to contact at least a part of both the gate electrode and the semiconductor layer.

13 Claims, 3 Drawing Sheets

OTHER PUBLICATIONS

Morvant et al., "In situ conductivity studies of poly (3,4-ethylenedioxythiophene)," *Synthetic Materials*, vol. 92, 1998, pp. 57-61.

Nilsson et al., "Bi-stable and Dynamic Current Modulation in Electrochemical Organic Transistors," *Advanced Materials*, vol. 14, No. 1, Jan. 4, 2002, pp. 51-54.

Taniguchi et al., "Vertical electrochemical transistor based on poly(3-hexylthiophene) and cyanoethylpullulan," *Applied Physics Letters*, vol. 85, No. 15, Oct. 11, 2004, pp. 3298-3300.

Chao et al., "Solid-State Microelectrochemistry: Electrical Characteristics of a Solid-State Microelectrochemical Transistor Based on Poly(3-methylthiophene)," *Journal of American Chemical Society*, vol. 109, No. 7, 1987, pp. 2197-2199.

Backlund et al., "Current modulation of a hygroscopic insulator organic field-effect transistor," *Applied Physics Letters*, vol. 85, No. 17, Oct. 25, 2004, pp. 3887-3889.

Panzer et al., "Low-voltage operation of a pentacene field-effect transistor with a polymer electrolyte gate dielectric," *Applied Physics Letters*, vol. 86, 2005, pp. 103503-1-103503-3.

Robinson et al., "On the Current Saturation Observed in Electrochemical Polymer Transistors," *Journal of the Electrochemical Society*, vol. 153, No. 3, 2006, pp. H39-H44.

Barsch et al., "Anodic Overoxidation of Polythiophenes in Wet Acetonitrile Electrolytes," *Electrochimica Acta*, vol. 41, No. 11/12, 1996, pp. 1761-1771.

Ohno et al., "Development of new class of ion conductive polymers based on ionic liquids," *Electrochimica Acta*, vol. 50, 2004, pp. 255-261.

Said et al., "Polymer field-effect transistor gated via a poly(styrenesulfonic acid) thin film," *Applied Physics Letters*, vol. 89, 2006, pp. 143507-1-143507-3.

\* cited by examiner

TRANSISTOR

FIELD OF THE INVENTION

Several aspects of the invention relate to field effect transistors that are gated with electrolytes. These transistors are particularly suitable for use in flexible, light-weight and reflective paper-like displays ("electronic paper").

BACKGROUND OF THE INVENTION

In "electronic paper" displays, an active matrix backplane based on Thin Film Transistors (TFTs) is used to address the display front-plane that contains the active display medium, which changes its optical properties in response to the application of an electric field (e.g. in liquid crystalline (LCD) or electrophoretic (EPD) displays), or the passage of electric current (e.g. in electrochromic displays, ECD).

Electrophoretic displays (EPDs) are electric field-driven, i.e. switching requires relatively large voltages (approx. 10V), but only very low current levels. An EPD based on a low-temperature polycrystalline silicon active matrix backplane has recently been presented [see SID International Symposium, Seminar, and Exhibition 2005, Boston, USA; paper 54.3: "A Flexible 2-in. QVGA LTPS-TFT Electrophoretic Display"; H. Kawai, M. Miyasaka, A. Miyazaki, T. Kodaira, S. Inoue, and T. Shimoda of Seiko-Epson Corp., Nagano, Japan, and K. Amundson, R. J. Paolini, Jr., M. D. McCreary, and T. H. Whitesides of E-Ink Corp., MA, USA].

An alternative technology for realizing active matrix backplanes is Organic Field Effect Transistor (OFET) technology, which is based on polymeric, oligomeric, or small molecular semiconducting organic materials. The charge carrier mobility in such organic semiconductors is several orders of magnitude lower than in high-performance inorganic semiconductors such as silicon, which results in correspondingly lower source-drain current levels. Furthermore, due to the larger thickness and lower dielectric constant of the polymeric dielectric layers in OFETs, the gate voltages required for turning the transistor on are higher as compared to silicon TFTs with thin $SiO_2$ dielectric layers. However, the performance of OFETs matches the requirements for driving electrophoretic displays in terms of driving voltage and current levels. Furthermore, an important advantage of OFETs as compared to silicon TFTs is that they can be produced using cost-effective printing technologies (pad, screen, or inkjet printing) for the additive patterning of device components. An example is the inkjet printing of semiconducting polymers to form a transistor channel between source and drain electrodes, and the inkjet printing of silver colloid to form gate electrode lines in top-gate polymer OFETs.

OFETs work in an accumulation mode, i.e. the charge carriers accumulate in the transistor channel in response to the gate voltage applied in the ON-state. In the OFF-state, when no gate voltage is applied, the residual charge carrier concentration (due to unintentional doping of the semiconductor) should be as low as possible in order to avoid crosstalk between neighboring pixels, and in order to maximize the bi-stability of the display pixel switching states.

In contrast to EPDs, electrochromic displays (ECDs) operate at very low driving voltages (0-2V), but require relatively high current levels for switching the pixel coloration states. An active matrix ECD demonstrator comprising inkjet-printed $TiO_2$-particle pixel electrodes, a viologen-based electrochrome, and a polycrystalline silicon TFT back-plane has recently been presented [see SID International Symposium, Seminar and Exhibition 2006, San Francisco, USA; paper 4.5: "The Design and Driving of Active-Matrix Electrochromic Displays Driven by LTPS TFTs", S. W-B. Tam, B. McGregor, and M. Ishida of Cambridge Research Laboratory of Epson, Cambridge, U.K., H. Kawai, S, Nebashi, and T. Shimoda of Seiko-Epson Corp., Nagano, Japan, and D. Corr, U. Bach, N. Leyland, F. Pichot, and P. Brien of NTERA, Ltd., Dublin, Ireland].

A major obstacle in using OFETs as switching transistors for ECDs is the low current output of OFETs. This results in prohibitively long switching times for updating the information content in ECDs based on OFETs.

As discussed above, the low current levels in OFETs are due to the low charge carrier mobility in most organic semiconductors, combined with a relatively low charge carrier concentration in the transistor ON-state. The latter is partly due to the large thickness and low dielectric constants of the dielectric polymer layers commonly used in OFETS. These factors lead to the specific capacitance of the transistor channel in OFETs being small in comparison to silicon TFTs, which also results in high gate voltages of the order of several tens of Volts being required for turning the transistor channel on. Lowering the gate voltage by reducing the thickness of the dielectric layer in an OFET is difficult because a thinner dielectric polymer layer results in increased leakage currents and the risk of a dielectric breakdown. Furthermore, whilst increasing the dielectric constant of the dielectric polymer results in an increased gate capacitance, it generally decreases the charge carrier mobility at the semiconductor-dielectric interface [see "Low-k Insulators as the Choice of Dielectrics in Organic Field-Effect Transistors", J. Veres, S. D. Ogier, S. W. Leeming, D. C. Cupertino, S. Mohialdin Khaffaf, Adv. Funct. Mat. 13, 199 (2003)].

Another problem encountered with OFETs is the fact that the charge carrier mobility of the organic semiconductor material is often decreased by the occurrence of a mixed semiconductor-insulator region at the semiconductor-dielectric interface. Thus, the solvents used for depositing successive layers of an OFET during device fabrication have to be carefully selected in order to minimize the intermixing at the interfaces (i.e. by choosing "orthogonal solvents"). Specifically, during the fabrication of OFETs, orthogonal solvents must be used for successively depositing the semiconductor layer (e.g. aromatic solvents for ADS2008 as supplied by "American Dye Source, Inc.", ADS), the dielectric layer (e.g. alcohol-based solvents for polyvinylphenol), and the gate electrode (e.g water-based PEDOT-PSS or silver colloids), without dissolving the preceding layers.

The above problem is particularly acute when the semiconductor material is soluble in a wide range of organic solvents. In this case, the formation of a sharp interface between the semiconductor and the dielectric layer, which is a pre-requisite for achieving high charge carrier mobility in OFETs, may be impossible.

Whereas the low current levels provided by OFETs are presently not sufficient to drive ECD pixels, an alternative technology based on electrochemical transistors (ECTs) has been demonstrated to provide high current levels. In such ECTs, the transistor channel is bridged by an electrochemically active, conducting polymer such as p-doped PEDOT-PSS. Adjacent to the conducting polymer layer, an electronically insulating but ionically conducting electrolyte layer in contact with a counter electrode ("gate electrode") allows an electric field to be applied to the electrochemically active material in the transistor channel (the "working electrode", in terms of electrochemistry), thus changing its oxidation state. When the conducting polymer is reduced from its p-doped (conducting) form to its neutral (semiconducting) form, the conductivity drops drastically.

ECTs based on conducting polymers, which are stable in their p-doped state, operate in a depletion mode. Prior to application of the gate voltage, the transistor is in an electrochemically stabilized ON-state, where negatively charged counterions are present in the bulk of the conjugated polymer, balancing the positive charges on the polymer chains, and thereby allowing for much higher charge carrier densities as compared to conventional OFETs in their ON-state. Due to this increased charge carrier density, ECTs can deliver much higher current levels than OFETs. Application of a positive gate voltage relative to the source contact switches the transistor channel from its initially p-doped ON-state to its electrochemically reduced OFF-state [see US2006202289, WO03047009, WO02071505 and SE0100748].

For p-doped PEDOT-PSS, conductivities in excess of 500 S/cm can be achieved [see H. Elschner of H. C. Starck GmbH, Germany, "High conductive PEDOT/PSS—a polymeric alternative to inorganic TCO"; presented at the "XIII$^{th}$. International Seminar: Commercial Applications of Conductive Polymers", Oct. 9-11, 2006, at the Villa La Pietra, Florence, Italy], while the conductivity drops to below 0.01 S/cm upon reduction to the neutral state of PEDOT [see J. R. Reynolds, and M. C. Morvant, Synth. Met. 92, 57 (1998)]. For ECTs based on PEDOT-PSS and operating with highly resistive electrolytes, ON/OFF ratios exceeding $10^5$ have been reported [see D. Nilsson, M. Chen, T. Kugler, T. Remonen, M. Armgarth, and M. Berggren, Adv. Mater. 14, 51 (2002)].

Another variant of ECTs is based on organic semiconductors that are stable in their neutral, non-doped state, i.e. the same organic semiconductor materials as are commonly used in OFETs [see T. Masateru and K. Tomoji, "Vertical electrochemical transistor based on poly(3-hexylthiophene) and cyanoethylpullulan", Appl. Phys. Lett. 85, 3298 (2004); S. Chao and M. S. Wrighton, "Solid State Microelectrochemistry: Electrical Characteristics of a Solid State Microelectrochemical Transistor Based on Poly(3-methylthiophene)", J. Am. Chem. Soc. 109, 6627 (1987); and T. G. Bäcklund, H. G. O, Sandberg, R. Österbacka, and H. Stubb, "Current modulation of a hygroscopic insulator organic field-effect transistor", Appl. Phys. Lett. 85, 3887 (2004)].

Furthermore, an electrochemical transistor based on a hydrogen-terminated diamond layer as an inorganic semiconductor which is gated by a water-based liquid electrolyte has been described in U.S. Pat. No. 6,833,059.

As in ECTs based on conducting polymers, the neutral organic semiconductor in the transistor channel is gated electrochemically with an electrolyte comprising mobile ions. However, these devices work in an accumulative mode, i.e. prior to the application of the gate voltage, the transistor is in its non-doped OFF-state. Applying a negative voltage to the gate (counter) electrode then results in electrochemical doping of the transistor channel and switching to the ON-state.

Both variants of ECTs have the benefit of operating at very small gate voltages (0V to −2V). The electrochemical doping and de-doping processes of the material in the transistor channel are driven by the potential applied between the gate (counter) electrode and the polymer in the transistor channel (working electrode). In contrast to OFETs, where the electric field extends throughout the dielectric layer between the transistor channel and the gate electrode, the electric field in electrolyte-gated ECTs is confined to the electrolytic double layer capacitances formed at the interfaces between the electrolyte and the transistor channel and gate electrode, respectively. As the specific capacitance of electrolytic double layers ($\mu F/cm^2$) is far larger than the specific capacitance in conventional OFETs ($nF/cm^2$), the gate voltages required for switching ECTs are drastically reduced as compared to OFETs [see M. J. Panzer, C. R. Newman, and C. D. Frisbie, "Low-voltage operation of a pentacene field-effect transistor with a polymer electrolyte gate dielectric", Appl. Phys. Lett. 86, 103503 (2005)].

Furthermore, the amplitude of the conductivity change in ECTs is independent of the distance between the gate electrode and the transistor channel, i.e. the thickness of the electrolyte layer. This allows lateral transistor configurations to be used, where the gate electrode is patterned from the same PEDOT-PSS layer as the source and drain contacts, at a distance of millimeters from a conjugated polymer channel [see D. Nilsson, M. Chen, T. Kugler, T. Remonen, M. Armgarth, and M. Berggren, "Bi-stable and Dynamic Current Modulation in Electrochemical Organic Transistors", Adv. Mater. 14, 51 (2002)].

The doping state within a conjugated polymer in the transistor channel of an ECT depends on its electrical potential relative to the potential of the surrounding electrolyte (which is controlled by the gate counter electrode). When a voltage is applied between the source and drain contacts, the difference between the electrical potential within the conjugated polymer and the surrounding electrolyte changes along the transistor channel. Consequently, the degree of doping within the transistor channel becomes a function of the position relative to the source and drain electrodes. This variation of the doping degree as a function of position results in a concomitant change of the local conductivity within the transistor channel, and the occurrence of current saturation (pinch-off) at low source-drain voltages (i.e. when the magnitude of the source-drain voltage $|V_{DS}|$ less than the magnitude of the gate voltage $|V_G|$) in the output characteristics of ECTs [see N. D. Robinson, P.-O. Svensson, D. Nilsson, and M. Berggren, "On the Current Saturation Observed in Electrochemical Polymer Transistors", J. Electrochem. Soc. 153H39 (2006)].

The use of electrolytes for addressing the transistor channel in ECTs, replacing the dielectric layer of OFETs, solves the problems of the low charge carrier concentrations and current levels of OFETs. Instead of dropping over the entire thickness of the dielectric layer, the potential difference between the gate electrode and the semiconductor material in the transistor channel of an ECT drops within the electrolytic double layer capacitances that are formed at the interfaces between the electrolyte and the gate electrode, and the electrolyte and the semiconductor in the transistor channel. As the thickness of these electrolytic double layer capacitances is far less than the thickness of the dielectric polymer layers commonly used in OFETs, the electric field strength within the electrolytic double layers, and hence the specific capacitance of the electrolytic double layers, are far larger than the electric field and the gate capacitance in conventional OFETs (of the order of $\mu F/cm^2$ instead of $nF/cm^2$). Correspondingly, the charge carrier concentration for a given gate voltage is drastically increased by the use of ECTs, and the gate voltages required for switching ECTs are drastically reduced as compared to OFETs.

Furthermore, the influx of counter-ions from the electrolyte into the bulk of the semiconductor in the transistor channel of an ECT during electrochemical doping stabilizes the charge carriers in the semiconductor material and thereby allows for even higher charge carrier concentrations.

However, a problem arises in the use of ECTs due to the electrochemical degradation of organic semiconductors in common electrolytes. The accumulation of holes (i.e. the formation of reactive carbo-cations, in chemical terminology) in the semiconductor material of an ECT at highly positive potentials often results in chemical reactions with species in the electrolyte, resulting in the disruption of the conjugated system and the irreversible loss of electrochemical activity. An example is the electrochemical degradation of polyaniline, which may occur very rapidly in aqueous electrolytes, due to nucleophilic attacks that result in the hydrolysis of the polymer chain.

Likewise, polythiophene films are easily "over-oxidised" in water-containing electrolytes, with both the degree of "over-oxidation" and the potential at which it occurs being highly dependent on the amount of water present in the electrolyte. The mechanism proposed to explain the "over-oxidation" of polythiophenes involves the oxidation of the sulphur atoms in the thiophene rings, followed by elimination of $SO_2$ [see "Anodic overoxidation of polythiophenes in wet acetonitrile electrolytes", Barsch, U. and F. Beck, Electrochimica Acta 41, 1761 (1996)].

In addition, the stability of the electrolyte itself is a major problem for electrochemical transistors (ECTs). Electrolytes need to have a constant, high ionic conductivity, a large electrochemical window within which the electrolyte is neither reduced nor oxidized at the cathode or anode, fast ion mobility during the redox intercalation/de-intercalation reactions, low volatility, and environmental stability.

Whilst proton-conductors allow for high ionic conductivities (e.g. Nafion displays 0.1 S/cm), acidic electrolytes are easily reduced at the cathode and result in the formation of hydrogen. Another issue with both water-based and organic solvent-based electrolytes is that they will eventually dry out and therefore require hermetic encapsulation to ensure a long device lifetime. The problem of solvent evaporation can be circumvented by using polymer-based solid electrolytes (such as Li salts dissolved in polyethylene oxide (PEO)). However, such solid electrolytes display comparatively low ionic conductivities.

A further problem with ECTs relates to their low operation frequencies and the occurrence of hysteresis during switching. The influx of counter-ions from the electrolyte into the bulk of the semiconductor in the transistor channel during the electrochemical doping of ECTs stabilizes the charge carriers in the semiconductor material. This provides the advantage of high charge carrier concentrations and high source-drain current levels in ECTs.

However, the disadvantage is that the diffusion of the counter-ions into the bulk of the semiconductor material limits the switching speed of ECTs. Furthermore, the electrochemical doping of the semiconductor in the transistor channel results in a memory effect, i.e. the ECT remains in the ON-state when a negative gate bias is first applied and then disconnected [see D. Nilsson, M. Chen, T. Kugler, T. Remonen, M. Armgarth, and M. Berggren "Bi-stable and Dynamic Current Modulation in Electrochemical Organic Transistors", Adv. Mater. 14, 51 (2002)].

Still another problem with electrolyte-gated ECTs is that ions can diffuse from the electrolyte into other device components. The performance of electric field-driven devices such as electrophoretic displays (EPDs) deteriorates in the presence of mobile ions, which result in ionic leakage currents and hysteresis effects. Therefore, great care has to be taken to encapsulate the electrolytes of ECTs when they are used in combination with electric field-driven devices.

Recently, an electrolyte-gated field-effect transistor based on a p-type semiconducting polymer that is gated via a polyanionic proton conductor has been developed [see E. Said et al., "Polymer field-effect transistor gated via a poly(styrenesulfonic acid) thin film, Appl. Phys. Lett. 89, 143507 (2006)]. In analogy to the ECTs based on semiconducting polymers described above, the application of very small gate voltages (less than 1V) is sufficient to result in the formation of large electrolytic double layer capacitances at the interfaces between the semiconductor-electrolyte and electrolyte-gate electrode interfaces. Hence the gate voltage required to switch the transistor on is very small.

However, as the electrolyte in this prior art transistor only comprises immobile polymeric anions that cannot diffuse into the bulk of the semiconductor layer, the (rate limiting) electrochemical doping and de-doping of the semiconductor layer that occurs in ECTs is prevented. This device is therefore not an electrochemical device, but rather a Field Effect Transistor (FET) gated by an electrolyte.

In combination with the high ionic conductivity of the proton conducting electrolyte, the prevention of electrochemical doping and de-doping allows for fast response times of the order of milliseconds, and corresponding device operation in the kHz frequency range, whilst maintaining the low driving voltages commonly observed for electrochemical transistors (ECTs). However, as the electrochemical doping of the transistor channel is prevented, the current levels in electrolyte-gated FETs are comparable to the low current levels in conventional OFETs.

The prior art electrolyte-gated FET suffers from very low charge carrier mobility. Furthermore, the transistor is limited to using a p-type semiconductor to form the transistor channel because the electrolyte is polyanionic. Hence, using an n-type semiconductor would allow electrochemical doping to occur in the channel, making the transistor an ECT rather than a FET. Finally, the acidic poly(styrenesulfonic acid) electrolyte used in the prior art electrolyte-gated FET tends to be reduced at the part of the transistor forming the cathode in use, forming hydrogen. This effect decreases the lifetime of the transistor.

SUMMARY OF THE INVENTION

According to an aspect of the present invention, there is provided an electrolyte-gated field effect transistor comprising an electrolyte including a polymeric ionic liquid analogue.

Throughout the description, the electrolyte material will be referred to as a polymeric ionic liquid. However, it should be understood that this term does not imply that the electrolyte material is necessarily a conventional free-flowing liquid. The electrolyte material need only be a polymeric ionic liquid analogue, including polymeric ionic materials that have an extremely high viscosity or even a rubber-like consistency.

Ionic liquids are salts that are molten over a wide temperature range, with a negligible vapor pressure at room temperature. Electrolytes based on polymeric ionic liquids will therefore not dry out, but maintain their ionic conductivity, in contrast to water-based and organic solvent-based electrolytes.

The driving voltages in polymeric ionic liquid-gated field effect transistors (PIL-FETs) according to the invention are lower than those of conventional polymer OFETs, and comparable to the low driving voltages seen in electrochemical transistors.

However, due to the polymeric nature of the electrolyte, the electrochemical doping of the transistor channel is prevented in PIL-FETs according to the invention. Therefore, their switching speeds are higher than those of electrochemical transistors. In addition, this allows for fast device operation without hysteresis, in contrast to the operation of ECTs.

Furthermore, as compared to conventional electrochemical transistors, PIL-FETs display both increased operational cycle lifetimes by avoiding the "over-oxidation" of the semiconductor in the transistor channel, and increased shelf-life-times by avoiding diffusion and the drying of the electrolyte. The prevention of electrochemistry in the transistor channel by the use of a polymeric ionic liquid electrolyte in accordance with the invention avoids over-oxidation, or over-reduction, of the semiconductor layer altogether. For example, in the case of a p-type conjugated polymer being used as the material for the semiconductor layer, ionic liquids comprising immobile polyanions do not allow for the diffusion of (negative) counter-ions into the bulk of the semiconductor material. Therefore electrochemical doping of the conjugated polymer is impossible, which also prevents the occurrence of electrochemical over-oxidation. Likewise, for n-type semiconductor materials such as metal oxides or metal chalcogenides, ionic liquids comprising immobile polycations prevent electrochemical over-reduction of the semiconductor material to the corresponding metal.

A further advantage arises due to the fact that electrolytes based on polymeric ionic liquids comprise one immobile ion component (either a polyanion or a polycation). This prevents the diffusion of ions from the electrolyte of a transistor according to the invention into other device components.

In addition, the problem of reduced charge carrier mobility due to intermixing experienced with OFETs can be avoided by replacing the dielectric layer with a polymeric ionic liquid for addressing the semiconductor material in the transistor channel, in accordance with the invention. Ionic liquids in general are known as "designer solvents" and allow for the fine-tuning of their solubility parameters. Thus, the solubility of the semiconductor layer of a transistor according to the invention in the polymeric ionic liquid used to gate the transistor can be minimized by an appropriate choice of the cation-anion combination in the polymeric ionic liquid.

Finally, the use of polymeric ionic liquids to gate a FET according to the invention solves the problems associated with the prior art electrolyte-gated FET. The inventor has found that transistors according to the invention have higher charge carrier mobility than the prior art electrolyte-gated FET, which is thought to be due to the lower polarity of the polymeric ionic liquid electrolytes compared to the proton conducting polyanionic electrolyte used in the prior art. Furthermore, appropriately selected polymeric ionic liquids can be used to gate transistors having either p-type or n-type transistor channels. In addition, polymeric ionic liquid electrolytes are more stable against oxidation and reduction than the prior art electrolyte, resulting in longer device lifetimes.

Preferably, the field effect transistor further comprises: a source electrode; a drain electrode disposed so as to be separated from the source electrode, forming a gap between the source and drain electrodes; a semiconductor layer bridging the gap between the source and drain electrodes and thus forming a transistor channel; and a gate electrode positioned so as to be separated from the source electrode, the drain electrode and the semiconductor layer; wherein the electrolyte is disposed so as to contact at least a part of both the gate electrode and the semiconductor layer.

Suitably, the polymeric ionic liquid analogue is electrochemically inert. Conveniently, the semiconductor layer comprises a p-type semiconductor material and the polymeric ionic liquid analogue comprises polymeric anions and mobile cations.

Preferably, the polymeric ionic liquid analogue comprises one or more cations selected from N-butyl-pyridinium, 1-ethyl-3-methylimidazolium, triethylsulphonium, N-methyl-N-trioctylammonium and N-butyl-N-methylpyrrolidinium. Suitably, the polymeric ionic liquid analogue comprises one or more poly-anions selected from poly[vinylsulfonate], poly[p-styrenesulfonate], poly[vinylphosphonate], and poly[3-sulfopropyl acrylate].

Conveniently, the polymeric ionic liquid analogue comprises poly-anionic brushes having alkyl, oligo-ethylene glycol, or oligo-propylene glycol spacers between an acid group and a polymerizable vinyl or acrylate group.

In one embodiment, the semiconductor layer comprises an n-type semiconductor material and the polymeric ionic liquid analogue comprises polymeric cations and mobile anions. Preferably, the polymeric ionic liquid analogue comprises one or more anions selected from tetrafluoroborate, hexafluorophosphate, trifluoromethylsulfonate and bis(trifluoromethylsulfonyl)imide.

Suitably, the polymeric ionic liquid analogue comprises one or more poly-cations selected from the poly[1-[2-(methacryloyloxy)dodecyl]-3-ethyl-imidazolium], poly[1-(p-vinylbenzyl)-3-methyl-imidazolium], poly[1-(p-vinylbenzyl)-3-butyl-imidazolium], poly[(p-vinylbenzyl)trimethyl ammonium], poly[(p-vinylbenzyl)triethyl ammonium], poly[(p-vinylbenzyl)tributyl ammonium], poly[2-(methacryloyloxy)ethyltrimethylamnonium], poly[(p-vinylbenzyl)triethyl phosphonium], poly[(p-vinylbenzyl)triphenyl phosphonium], poly[p-vinylbenzyl)pyridinium], poly[bis(2-hydroxyethyl)dimethyl ammonium], poly[2,2-bis(methylimidazolium methyl)-1,3-propanediol], and poly[2,2-bis(butylimidazolium methyl)-1,3-propanediol] cations.

Preferably, the semiconductor layer comprises a p-type semiconductor material selected from an organic material, a metal-organic complex and an inorganic material. Suitably, the p-type semiconductor material is an organic material and is one of a material comprising small molecules, an oligomeric material and a polymeric material.

Conveniently, the semiconductor material comprises pentacene, phthalocyanine, tetrabenzoporphyrine, (biphenyl) tetrathiafulvalene or analogues of these compounds. Alternatively, the semiconductor material comprises di-hexyl quaterthiophene, alpha-sexithiophene, a thiophene-phenylene oligomer, or a thiophene-thiazole oligomer. In one embodiment, the semiconductor material comprises poly[3-hexylthiophene], poly[5,5'-bis(3-dodecyl-2-thienyl)-2,2'-bithiophene] or poly[9,9-dioctylfluorene-co-bithiophene].

Suitably, the p-type semiconductor material is a metal-organic complex and is one of an oligomeric material, a polymeric material and a material comprising small molecules. Preferably, the semiconductor material comprises Cu-phthalocyanine, Mg-phthalocyanine or Zn-phthalocyanine. Alternatively, the semiconductor material comprises Si-phthalocyanine or Ru-phthalocyanine.

Preferably, the p-type semiconductor material is inorganic and comprises one of a metal oxide and a metal chalcogenide. Suitably, the p-type semiconductor material comprises silver oxide ($Ag_2O$), cuprous oxide ($Cu_2O$), cupric oxide (CuO), zinc oxide (ZnO), or a perovskite. Conveniently, the p-type semiconductor material comprises $SrFe_yCo_{1-y}O_{2.5+x}$ (y=0.5) or $SrTi_{(0.8)}Fe_{(0.2)}O_{(3-\square)}$.

Alternatively, the p-type semiconductor material comprises copper(I)sulphide ($Cu_2S$), copper(I)selenide ($Cu_2Se$), copper indium selenide $CuInSe_2$, or CIGS ($Cu(InGa)Se_2$).

Suitably, the p-type semiconductor material is inorganic and comprises carbon nano tubes (CNTs).

Conveniently, the semiconductor layer comprises an n-type semiconductor material selected from an organic material, a metal-organic complex and an inorganic material. Preferably, the n-type semiconductor material is organic and is one of a material comprising small molecules, an oligomeric material and a polymeric material. Suitably, the n-type semiconductor material comprises perylenetetracarboxylicacid dianhydride (PTCDA), dimethylperylenetetracarboxylicacid diimide (MePTCDI), fullerene (C60), C60-fused pyrrolidine-meta-C12 phenyl (C60MC12), or [6,6]-phenyl C61-butyric acid methyl ester (PCBM).

Alternatively, the n-type semiconductor material comprises a thiazole oligomer with 4-trifluormethylphenyl groups, a thiazole/thiophene co-oligomer with 4-trifluormethylphenyl groups, a perfluoroarene-capped oligothiophene such as 5,5''-diperfluorophenyl-2,2':5',2'':5'',2'''-quaterthiophene, or a perfluorinated phenylene dendrimer. Preferably, the n-type semiconductor material comprises C60F42 or C132F90.

In one embodiment, the n-type semiconductor material comprises polybenzimidazobenzophenanthroline (BBL) or poly[2-methoxy-5-(2'-ethylhexyloxy)-1,4-(1-cyanovinylene)phenylene] (MEH-CN-PPV).

Suitably, the n-type semiconductor material is a metal-organic complex and is a material comprising small molecules. Preferably, the n-type semiconductor material comprises perfluoro-vanadyl-phthalocyanine, perfluoro-copper-phthalocyanine, tetrapyridotetraazaporphyrinato zinc(II) (TPyTAPZn), tris(8-quinolinolato)aluminium ($Alq_3$), tris(4-methyl-8-quinolinolato)aluminium ($Almq_3$), bis(10-hydroxybenzo[h]-quinolinato)beryllium ($BeBq_2$), bis(2-methyl-8-quinolinolato)-(4-hydroxy-biphenylyl)-aluminium (BAlq), bis[2-(2-hydroxyphenyl)-benzoxazolato]zinc (Zn $(BOX)_2$) or bis[2-(2-hydroxyphenyl)-benzothiazolato]zinc ($Zn(BTZ)_2$).

Suitably, the n-type semiconductor material is an inorganic material and comprises one of a metal oxide and a metal chalcogenide. Preferably, the n-type semiconductor material comprises tungsten trioxide ($WO_3$), titanium dioxide ($TiO_2$), zinc oxide ($ZnO_2$), tin oxide ($SnO_2$) or indium tin oxide (ITO). Alternatively, the n-type semiconductor material comprises tin sulphide ($SnS_2$), cadmium sulphide (CdS) or cadmium selenide (CdSe).

Preferably, the source, drain and gate electrodes are made of an electrochemically inert material. Conveniently, the source, drain and gate electrodes are made from gold, platinum, palladium or a conducting form of carbon. Suitably, the area of an interface between the gate electrode and the electrolyte is larger than the area of an interface between the electrolyte and the semiconductor layer, the former interface having a larger capacitance than the latter. Preferably, a surface of the gate electrode in contact with the electrolyte is porous. More preferably, the surface of the gate electrode comprises a material in the form of nano-particles or nano-tubes.

Suitably, the specific conductivity of the electrolyte exceeds $10^{-6}$ S/cm.

Preferably, the field effect transistor further comprises an encapsulating layer encapsulating the electrolyte.

Conveniently, the field effect transistor has an operational voltage less than 2V.

BRIEF DESCRIPTION OF THE DRAWINGS

Embodiments of the present invention will now be described by way of further example only and with reference to the accompanying drawings, in which.

DETAILED DESCRIPTION

Figure 1:
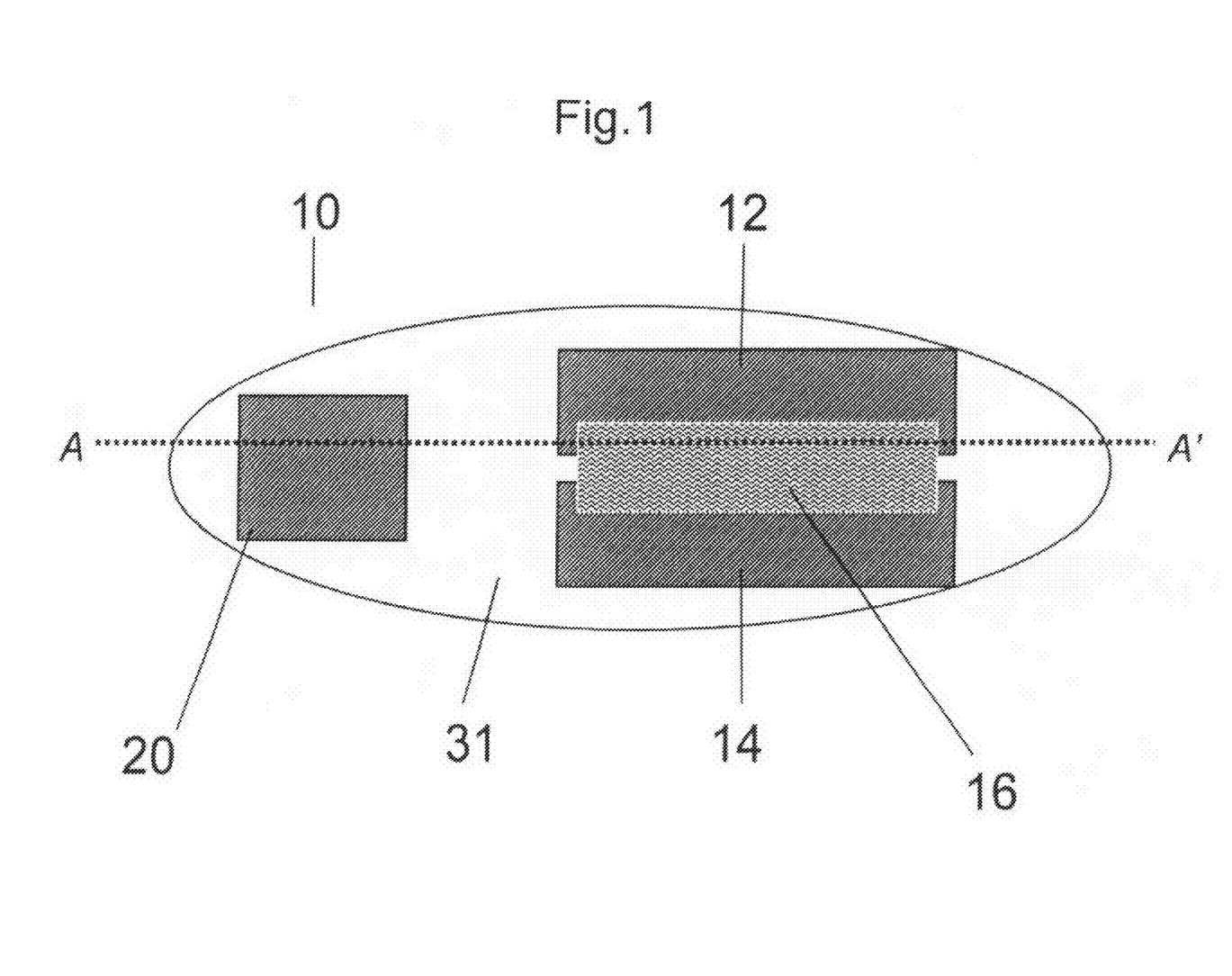
FIG. 1 shows a top view of the basic elements of a Polymeric Ionic Liquid-gated Field Effect Transistor (PIL-FET) according to an embodiment of the invention.

FIG. 1 shows a top view of the basic elements of a Polymeric Ionic Liquid-gated Field Effect Transistor (PIL-FET). A source electrode 12 and a drain electrode 14 are fabricated on an insulating substrate 10 and separated by a gap, which defines the transistor channel. A layer of a semiconductor material 16 bridges the gap between the source and drain electrodes 12, 14 and thus forms the transistor channel. A gate electrode 20 is positioned in close proximity to the source and drain electrodes 12, 14. An electrolyte layer 31 comprising a polymeric ionic liquid is in contact with the gate electrode 20 and completely covers the semiconductor material 16 in the transistor channel.

In the following, the possible material choices for the basic elements of the PIL-FET displayed in FIG. 1 are discussed:
(A) Source, Drain and Gate Electrodes The source, drain, and gate electrodes 12, 14, 20 are preferably made from an electrochemically inert material such as gold, platinum, palladium, or a conductive form of carbon, in order to prevent electrochemical corrosion during operation whilst in contact with the electrolyte 31.
(B) Material Choices for the Semiconductor Material in the Transistor Channel The semiconductor material 16 in PIL-FETs may be p-type or n-type. Also, the transistor channel in PIL-FETs may comprise a single semiconductor material or a combination of several, p-type or n-type, semiconductor materials. The semiconductor material(s) may be inorganic, metal-organic, or organic, and may comprise small molecules, oligomers, or polymers.
(B1) p-Type Semiconductor Materials The semiconductor 16 in the transistor channel may be a p-type organic semiconductor material comprising small molecules such as pentacene, phthalocyanine, tetrabenzoporphyrine, or (biphenyl)tetrathiafulvalene. Alternatively, the p-type organic semiconductor material may be an oligomer such as di-hexyl quaterthiophene, alpha-sexithiophene, a thiophene-phenylene oligomer, or a thiophene-thiazole oligomer. Also, the p-type organic semiconductor material may be a polymer such as poly[3-hexylthiophene] (P3HT), poly[5,5'-bis(3-dodecyl-2-thienyl)-2,2'-bithiophene] (PQT-12), or poly[9,9-dioctylfluorene-co-bithiophene] (ADS2008).

Other possible p-type semiconductor materials for PIL-FETs include metal-organic complexes such as Cu-phthalocyanine, Mg-phthalocyanine, or Zn-phthalocyanine. Furthermore, such metal organic complexes may be oligomeric, as in Si-phthalocyanine or Ru-phthalocyanine, or even polymeric.

Furthermore, the p-type semiconductor material may be inorganic and comprise a metal oxide such as silver oxide ($Ag_2O$), cuprous oxide ($Cu_2O$), cupric oxide (CuO), zinc oxide (ZnO), or a perovskite such as $SrFe_yCo_{1-y}O_{2.5+x}$ (y=0.5), or $SrTi_{(0,8)}Fe_{(0,2)}O_{(3-\square)}$.

Also, the p-type semiconductor material may comprise a metal chalcogenide such as copper(I)sulphide ($Cu_2S$), copper (I)selenide ($Cu_2Se$), copper indium selenide ($CuInSe_2$), or CIGS ($Cu(InGa)Se_2$).

Finally, the p-type semiconductor material may be in elemental form such as carbon nano-tubes (CNTs).
(B2) n-Type Semiconductor Materials Furthermore, the semiconductor 16 in the transistor channel may be an n-type organic semiconductor material comprising small molecules such as perylenetetracarboxylicacid dianhydride (PTCDA), dimethylperylenetetracarboxylicacid diimide (MePTCDI), fullerene ($C_{60}$), $C_{60}$-fused pyrrolidine-meta-$C_{12}$ phenyl (C60MC12), or [6,6]-phenyl $C_{61}$-butyric acid methyl ester (PCBM). The n-type organic semiconductor material may also be oligomeric comprising thiazole oligomers with 4-trifluormethylphenyl groups, thiazole/thiophene co-oligomers with 4-trifluormethylphenyl groups, perfluoroarene-capped oligothiophenes such as 5,5"-diperfluorophenyl-2,2':5',2":5",2'''-quaterthiophene, or perfluorinated phenylene dendrimers such as $C_{60}F_{42}$ or $C_{132}F_{90}$. Also, the n-type organic semiconductor material may be a polymer such as polybenzimidazobenzophenanthroline (BBL) or poly [2-methoxy-5-(2'-ethylhexyloxy)-1,4-(1-cyanovinylene) phenylene (MEH-CN-PPV).

Other possible n-type semiconductor materials for PIL-FETs include metal-organic complexes such as perfluoro-vanadyl-phthalocyanine, perfluoro-copper-phthalocyanine, tetrapyridotetraazaporphyrinato zinc(II) (TPyTAPZn), tris (8-quinolinolato)aluminium ($Alq_3$), tris(4-methyl-8-quinolinolato)aluminium ($Almq_3$), bis(10-hydroxybenzo[h]-quinolinato)beryllium ($BeBq_2$), bis(2-methyl-8-quinolinolato)-(4-hydroxy-biphenylyl)-aluminium (BAlq), bis[2-(2-hydroxyphenyl)-benzoxazolato]zinc ($Zn(BOX)_2$), or bis[2-(2-hydroxyphenyl)-benzothiazolato]zinc ($Zn(BTZ)_2$).

The n-type semiconductor material may also be an inorganic metal oxide such as tungsten trioxide ($WO_3$), titanium dioxide ($TiO_2$), zinc oxide ($ZnO_2$), tin oxide ($SnO_2$), or indium tin oxide (ITO), or a metal chalcogenide such as cadmium sulphide (CdS) or cadmium selenide (CdSe).

(C) Polymeric Ionic Liquid-Based Electrolyte

In contrast to electrochemical transistors, PIL-FETs are electrolyte-gated field effect transistors in which the electrochemical doping of the semiconductor material in the transistor channel is prevented.

The electrolyte 31 in PIL-FETs must therefore be chosen to display a large window of electrochemical stability, i.e. the polymeric ionic liquid of the electrolyte 31 must only comprise cations with a low electron affinity (which are difficult to reduce), and anions with a high ionisation potential (that are difficult to oxidise).

Furthermore, the polymeric ionic liquid may be chosen to either comprise immobile, polymeric anions in combination with mobile cations, or immobile, polymeric cations in combination with mobile anions.

The choice of the cation/anion combination in the polymeric ionic liquid depends on the conductivity type of the semiconductor material 16 in the transistor channel. The electrochemical doping of a neutral semiconductor material in the transistor channel requires the insertion of counter-ions from the electrolyte 31 into the bulk of the neutral semiconductor. Correspondingly, the de-doping of a doped semiconductor results in the release of counter-ions from the bulk of the doped semiconductor into the electrolyte 31.

Specifically, p-doping (i.e. the electrochemical oxidation) of a semiconductor 16 in the transistor channel requires the insertion of anions from the electrolyte 31 into the bulk of the semiconductor 16. Therefore, when a p-type semiconductor layer is used for the transistor channel of a PIL-FET, the polymeric ionic liquid electrolyte 31 must not comprise any mobile anions in order to prevent the electrochemical oxidation of the semiconductor layer 16. PIL-FETs having p-type semiconductor layers require an electrolyte 31 comprising immobile, polymeric anions in combination with mobile cations.

In contrast, in the case of a PIL-FET having an n-type semiconductor layer, the electrolyte 31 must not comprise any mobile protons or other cations in order to prevent the electrochemical reduction of the semiconductor layer 16. Therefore, PIL-FETs having n-type semiconductor layers require an electrolyte 31 comprising immobile, polymeric cations in combination with mobile anions.

(C1) Polymeric Ionic Liquid Electrolytes for p-Type Semiconductors

The polymeric ionic liquid electrolytes 31 for PIL-FETS having p-type semiconductor layers may be chosen to comprise electrochemically stable, mobile cations identical or equivalent to N-butyl-pyridinium, 1-ethyl-3-methylimidazolium, triethylsulphonium, N-methyl-N-trioctylammonium, or N-butyl-N-methylpyrrolidinium.

As for the anion component, the polymeric ionic liquid may comprise immobile poly-anions such as poly[vinylsulfonate], poly[p-styrenesulfonate], poly[vinylphosphonate], or poly[3-sulfopropyl acrylate], or poly-anionic brushes with alkyl, oligo-ethylene glycol, or oligo-propylene glycol spacers between the acid group and the polymerizable vinyl or acrylate group.

(C2) Polymeric Ionic Liquid Electrolytes for N-Type Semiconductors

The polymeric ionic liquid electrolytes 31 for PIL-FETs having n-type semiconductor layers may be chosen to comprise electrochemically stable, mobile anions identical or equivalent to tetrafluoroborate, hexafluorophosphate, trifluoromethylsulfonate, or bis(trifluoromethylsulfonyl)imide.

As for the cation component, the polymeric ionic liquid may comprise immobile poly-cations such as the poly[1-[2-(methacryloyloxy)dodecyl]-3-ethyl-imidazolium], poly[1-(p-vinylbenzyl)-3-methyl-imidazolium], poly[1-(p-vinylbenzyl)-3-butyl-imidazolium], poly[(p-vinylbenzyl) trimethyl ammonium], poly[(p-vinylbenzyl)triethyl ammonium], poly[(p-vinylbenzyl)tributyl ammonium], poly [2-(methacryloyloxy)ethyltrimethylamnonium], poly[(p-vinylbenzyl)triethyl phosphonium], poly[(p-vinylbenzyl) triphenyl phosphonium], poly[p-vinylbenzyl) pyridinium], poly[bis(2-hydroxyethyl)dimethyl ammonium], poly[2,2-bis (methylimidazolium methyl)-1,3-propanediol], or poly[2,2-bis(butylimidazolium methyl)-1,3-propanediol] cations.

Both for PIL-FETs having p-type semiconductor layers and PIL-FETs having n-type semiconductor layers, the combination of anions and cations in the polymeric ionic liquid electrolyte 31 should be chosen such that the specific conductivity of the electrolyte exceeds $10^{-6}$ S/cm, or preferably $10^{-4}$ S/cm, or most preferably $10^{-2}$ S/cm.

Figure 2:
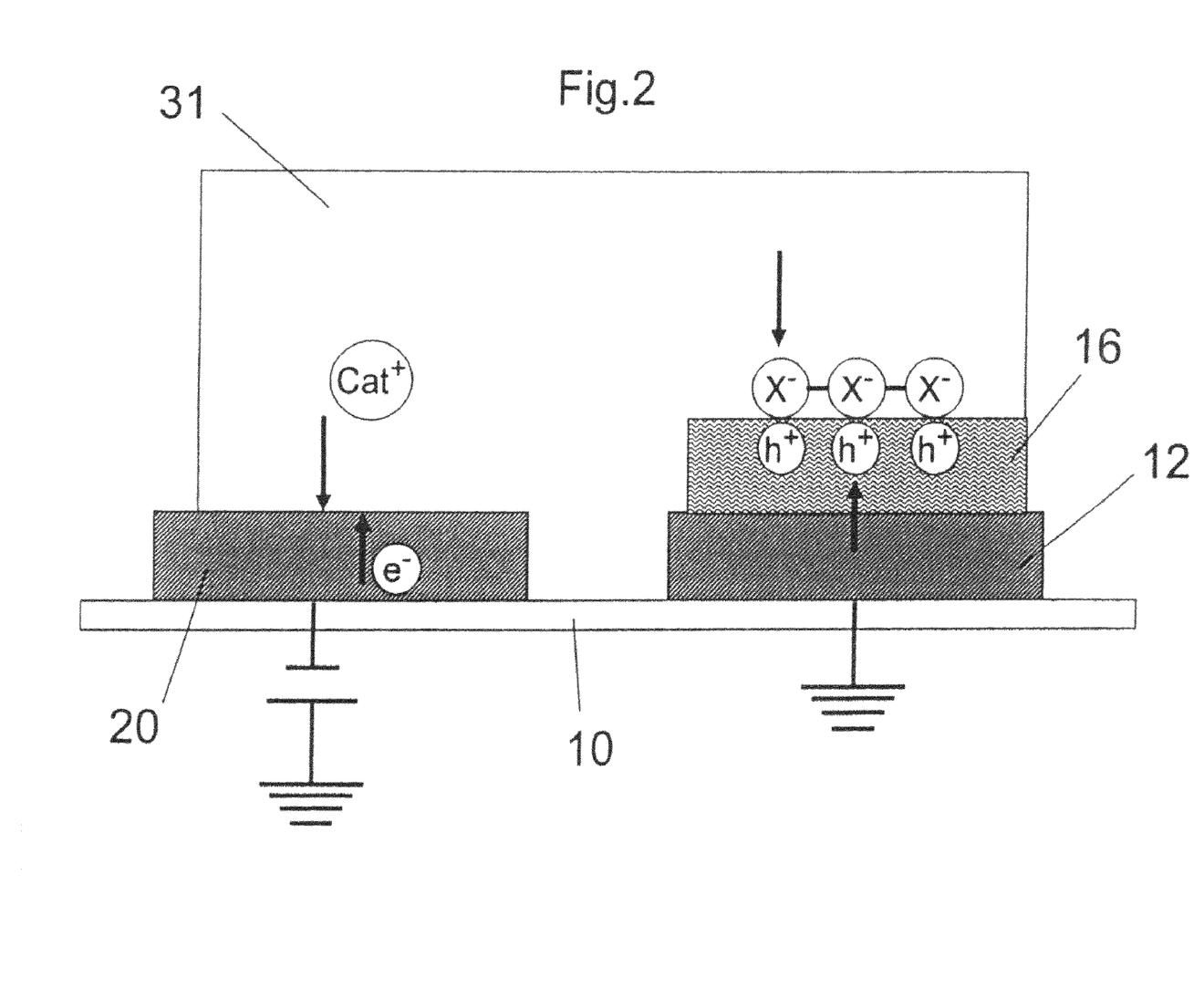
FIG. 2 shows a cross-section, along the line A-A' in FIG. 1, of a p-type PIL-FET according to an embodiment of the invention.

FIG. 2 shows a cross-section of a p-type PIL-FET taken along the line (A-A') in FIG. 1, the PIL-FET being in its ON-state. Application of a negative gate voltage results in the diffusion of cations ($Cat^+$) from the polymeric ionic liquid electrolyte 31 to the negatively charged gate electrode 20, which results in the formation of an electrolytic double layer capacitance at the gate electrode-electrolyte interface.

Simultaneously, polyanions ($X^-$-$X^-$-$X^-$) diffuse from the bulk of the polymeric ionic liquid electrolyte 31 to the interface with the p-type semiconductor layer 16, which bridges the source electrode 12 and drain electrode 14 (not included in FIG. 2). Correspondingly, positive charge carriers $h^+$ (holes) accumulate in the p-type semiconductor layer 16 at the interface with the electrolyte 31.

This accumulation of polymeric anions and holes at the electrolyte-semiconductor interface forms an electrolytic double layer capacitance. PIL-FETs therefore allow device operation at very low gate voltages ($V_G$=0 to −2V) in an analogous way to electrochemical transistors.

Due to their macromolecular nature, polymeric anions cannot diffuse into the bulk of the p-type semiconductor 16. Thus, in contrast to an electrochemical transistor, the electrochemical oxidation of the bulk of the semiconductor 16, which requires the insertion of counter-anions, is not possible in a PIL-FET using a polyanion-based electrolyte 31. PIL-FETs are therefore field-effect transistors rather than electrochemical transistors. Correspondingly, PIL-FETs allow for higher switching speeds than electrochemical transistors. Furthermore, the current levels in PIL-FETS in their ON-state are restricted to the current levels typically observed in OFETs.

Figure 3:
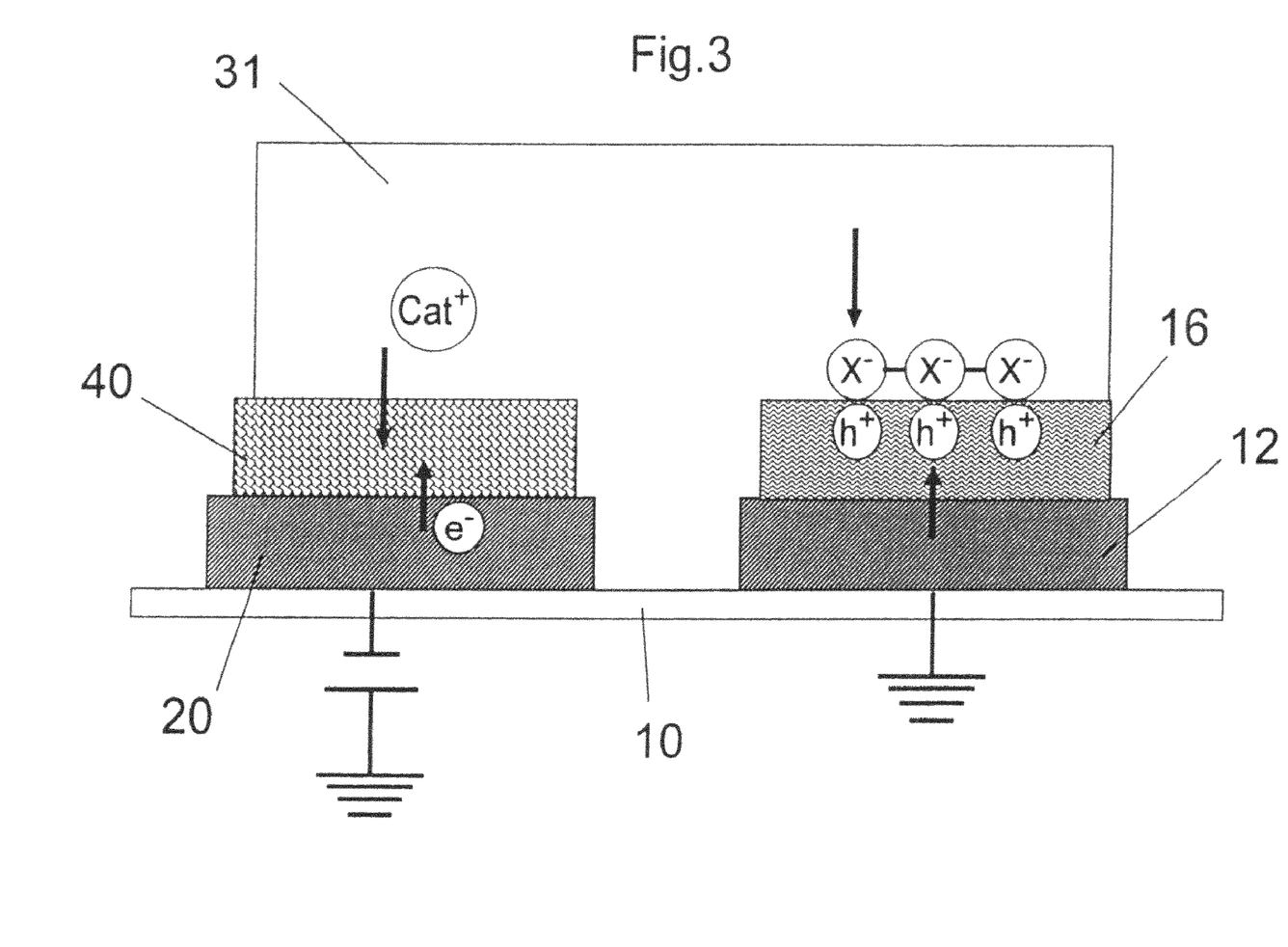
FIG. 3 shows a cross-section of a p-type PIL-FET according to an embodiment of the invention that includes an ion storage layer deposited onto the gate electrode.

FIG. 3 shows a cross-section of a p-type PIL-FET that includes an ion storage layer 40 deposited onto the gate electrode 20. Application of a negative gate voltage results in the diffusion of cations $Cat^+$ from the polymeric ionic liquid electrolyte 31 into the ion storage layer 40. The function of the ion storage layer 40 is to ensure a fast counter-balancing of the formation of the electrolytic double layer capacitance at the semiconductor-electrolyte interface.

The ion storage layer 40 may comprise an electrochemically inert material with a large surface area. Examples include nano-particulate carbon (i.e. carbon black). Such a capacitive ion storage layer 40 results in the fast formation of an electrolytic double layer capacitance at the gate-electrolyte interface.

In general, the area of the gate electrode 20 in contact with the electrolyte 31 should be equal to or larger than the combined areas in contact with the electrolyte 31 of the source electrode 12, the transistor channel 16, and the drain electrode 14.

Alternatively, the ion storage layer 40 may be based on electrochemically active materials.

As in FIG. 2, at the same time as the diffusion of cations to the gate 20 having the ion storage layer 40, polyanions ($X^-$-$X^-$-$X^-$) diffuse from the bulk of the polymeric ionic liquid electrolyte 31 to the interface with the p-type semiconductor layer 16, which bridges the source electrode 12 and the drain electrode 14 (not included in FIG. 3). Correspondingly, positive charge carriers h (holes) accumulate in the p-type semiconductor layer 16 at the interface with the electrolyte 31.

This accumulation of polymeric anions and holes at the electrolyte-semiconductor interface forms an electrolytic double layer capacitance. PIL-FETs therefore allow device operation at very low gate voltages ($V_G$=0 to $-2V$) in an analogous way to electrochemical transistors.

FIRST EXAMPLE

PIL-FET Based on a p-Type Semiconducting Polymer

In this example of a PIL-FET, the semiconductor layer was chosen to be p-type. The source, drain and gate electrodes were patterned from an evaporated gold layer on a glass substrate. The channel length L was 20 µm, and the width W was 1 mm. The gate electrode was positioned laterally to the source-drain electrode pair on the substrate, at a distance of 1 mm.

The source and drain electrodes were bridged by a 40 nm thick pattern of the p-type organic fluorene-bithiophene copolymer ADS2008 (supplied by American Dye Source, Inc.), which forms the transistor channel.

The electrolyte consisted of the polymeric ionic liquid 1-ethyl-3-methylimidazolium poly[vinylsulfonate], synthesized according to the procedure reported by H. Ohno et al., Electrochimica Acta 50, 255-261 (2004).

SECOND EXAMPLE

PIL-FET Based on an n-Type Inorganic Semiconductor, Comprising a Capacitive Counterelectrode In this example of a PIL-FET the semiconductor layer was chosen to be n-type. The source, drain, and gate electrodes were patterned from an evaporated gold layer on a glass substrate. The channel length L was 20 µm, and the width W was 1 mm. The gate electrode was positioned laterally to the source-drain electrode pair on the substrate, at a distance of 1 mm.

A 200 nm thick layer of carbon black was deposited on top of the gate electrode. The source and drain electrodes were bridged by a 30 nm thick pattern of the n-type inorganic semiconductor tin(IV)sulfide ($SnS_2$), forming the transistor channel.

The electrolyte consisted of the polymeric ionic liquid poly[1-[2-(methacryloyloxy)dodecyl]-3-ethyl-imidazolium] bis(trifluoromethylsulfonyl)imide, synthesized according to the procedure reported by H. Ohno et al., Electrochimica Acta 50, 255-261 (2004).

Due to the large surface area of the carbon black ion storage layer in contact with the electrolyte, in a PIL-FET as in this example the footprint of the gate electrode may be made much smaller than the combined areas of the source electrode, the transistor channel, and the drain electrode that are in contact with the electrolyte.

The main effect of gating field effect transistors with electrolytes based on polymeric ionic liquids (PIL-FETs) is that their driving voltages are reduced compared to conventional polymer OFETs, and are comparable to the very low driving voltages observed for electrochemical transistors.

Another effect of using polymeric ionic liquids to gate FETs is to prevent electrochemical doping of the semiconductor material in the transistor channel. Therefore, the switching speeds of PIL-FETs are higher than those of electrochemical transistors, and their source-drain current levels are of the same order of magnitude as in OFETs.

Furthermore, the reduction of charge carrier mobility due to intermixing at the semiconductor-polymer dielectric interface in OFETs is avoided by replacing the dielectric layer with a polymeric ionic liquid for addressing the semiconductor material in the transistor channel. The solubility of the semiconductor layer in the polymeric ionic liquid used to gate the PIL-FET can be minimized by an appropriate choice of the cation-anion combination in the polymeric ionic liquid.

Another effect of the invention is that, compared to other electrochemical transistors based on conjugated organic materials, the replacement of water-based or solid polymer-based electrolytes with polymeric ionic liquid-based electrolytes avoids the occurrence of electrochemistry in the transistor channel and thereby drastically increases the operational cycle lifetime of the transistors by avoiding effects such as "over-oxidation" of the semiconductor material in the transistor channel.

Also, the invention increases the shelf-lifetime of systems that combine electrolyte-gated FETs with electric field-driven devices compared to systems using prior art electrolyte-gated FETs. Electrolytes based on polymeric ionic liquids comprise one immobile ion component (i.e. either a polyanion or a polycation), which prevents the diffusion of the electrolyte into other device components.

Prior art electrolyte-gated FETs suffer from low charge carrier mobility. This problem has been found to be mitigated by the use of polymeric ionic liquids as electrolytes in electrolyte-gated FETs, possibly due to the low polarity of polymeric ionic liquids. Furthermore, by choosing an appropriate anion-cation combination, polymeric ionic liquids can be suitable for use with either p-type or n-type transistor channels, whereas prior art electrolyte-gated FETs can only operate with a p-type channel, which is not suitable for all applications. In addition, the operational lifetime of PIL-FETs is increased compared to prior art electrolyte-gated FETs because polymeric ionic liquids have a large window of electrochemical stability and so are not reduced or oxidized in operation. In contrast, the acidic electrolyte used in prior art electrolyte-gated FETs is easily reduced to form hydrogen, degrading the transistor in use.

Finally, an additional factor that increases the shelf-lifetimes of PIL-FETs as compared to devices comprising water-based or organic solvent-based electrolytes is the fact that polymeric ionic liquids are non-volatile.

The aforegoing description has been given by way of example only and it will be appreciated by a person skilled in the art that modifications can be made without departing from the scope of the present invention.

What is claimed is:

1. A transistor, comprising:
a source electrode;
a drain electrode;
a semiconductor material contacting the source electrode and the drain electrode, the semiconductor material including a p-type semiconductor material;
an electrolyte contacting the semiconductor material, the electrolyte including polymeric anions and mobile cations; and
a gate electrode contacting the electrolyte,
wherein the electrolyte includes a polymeric ionic liquid analog, the polymeric ionic liquid analog comprising one or more cations selected from N-butyl-pyridinium, 1-ethyl-3-methylimidazolium, triethylsulphonium, N-methyl-N-trioctylammonium and N-butyl-N-methylpyrrolidinium.

2. The transistor according to claim 1, further comprising:
a substrate on which the gate electrode, the source electrode and the drain electrode are disposed.

3. The transistor according to claim 2, the electrolyte covering the semiconductor material and the gate electrode.

4. The transistor according to claim 1, each of the gate electrode, the source electrode and the drain electrode including an electrochemically inert metal.

5. The transistor according to claim 1, the semiconductor material including pentacene, phthalocyanine, tetrabenzoporphyrine, (biphenyl)tetrathiafulvalene or analogues of these compounds.

6. The transistor according to claim 1, the semiconductor material including di-hexyl quaterthiophene, alpha-sexithiophene, a thiophene-phenylene oligomer, or a thiophene-thiazole oligomer.

7. The transistor according to claim 1, the semiconductor material including poly[3-hexylthiophene], poly[5,5'-bis(3-dodecyl-2-thienyl)-2,2'-bithiophene] or poly[9,9-dioctylfluorene-co-bithiophene].

8. The transistor according to claim 1, the electrolyte including an ionic material that has a rubber-like consistency.

9. The transistor according to claim 1, the semiconductor material being porous.

10. The transistor according to claim 1, further comprising:
an encapsulating layer encapsulating the electrolyte.

11. An electrochromic display device comprising:
the transistor according to claim 1.

12. An electronic paper comprising:
an active matrix backplane including the transistor according to claim 1.

13. A transistor, comprising:
a source electrode;
a drain electrode;
a p-type semiconductor material contacting the source electrode and the drain electrode;
an electrolyte contacting the semiconductor material, the electrolyte including polymeric anions and mobile cations; and
a gate electrode contacting the electrolyte, the gate electrode being electrochemically inert,
wherein the electrolyte includes a polymeric ionic liquid analog, the polymeric ionic liquid analog comprising one or more cations selected from N-butyl-pyridinium, 1-ethyl-3-methylimidazolium, triethylsulphonium, N-methyl-N-trioctylammonium and N-butyl-N-methylpyrrolidinium.

* * * * *